US00PP28485P2

(12) United States Plant Patent
Heemskerk

(10) Patent No.: US PP28,485 P2
(45) Date of Patent: Oct. 3, 2017

(54) ***HEMEROCALLIS* PLANT NAMED 'VER00323'**

(50) Latin Name: ***Hemerocallis* hybrid**
Varietal Denomination: VER00323

(71) Applicant: Gerardus J. C. M. Heemskerk, Noordwijk (NL)

(72) Inventor: Gerardus J. C. M. Heemskerk, Noordwijk (NL)

(73) Assignee: HEEMS KERK VASTE PLANTENBV, Noordwijk (NL)

( * ) Notice: Subject to any disclaimer, the term of this patent is extended or adjusted under 35 U.S.C. 154(b) by 126 days.

(21) Appl. No.: 14/756,937

(22) Filed: Oct. 30, 2015

(51) Int. Cl.
*A01H 5/02* (2006.01)

(52) U.S. Cl.
USPC ..... Plt./312

(58) Field of Classification Search
USPC ..... Plt./263.1, 312
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Hemerocallis* named 'VER00323' that is characterized by its flowers that are salmon orange in color with a yellow-green throats, its everblooming habit; blooming from June to October in The Netherlands, its dormant plant habit, and its early commencement of bloom in the season.

2 Drawing Sheets

Botanical classification: *Hemerocallis* hybrid.
Cultivar designation: 'VER00323'.

BACKGROUND OF THE INVENTION

The present invention relates to a new and distinct cultivar of *Hemerocallis* plant of hybrid origin, botanically known as *Hemerocallis* 'VER00323' and will be referred to hereafter by its cultivar name, 'VER00323'.

The new cultivar was developed through an on-going breeding program conducted by the Inventor in Noordwijk, The Netherlands. The objectives of the breeding program are to develop new cultivars of *Hemerocallis* that are everblooming with compact plant habits in a range of flower colors.

The new cultivar arose from crosses made in summer of 2006. Proprietary seed parent lines were pollinated with a mixture of pollen collected from proprietary pollen parents and the collected seeds were pooled and sown for evaluation. 'VER00323' was selected as a single unique plant from the resulting seedlings in summer of 2009. The specific parents are unknown and none of the possible parent plants are named or patented.

Asexual propagation of the new cultivar was first accomplished by division in Noordwijk, The Netherlands in 2009 by the Inventor. Asexual propagation by division and tissue culture has determined that the characteristics of this cultivar are stable and are reproduced true to type in successive generations.

SUMMARY OF THE INVENTION

The following traits have been repeatedly observed and represent the characteristics of 'VER00323'. These attributes in combination distinguish 'VER00323' as a new and distinct cultivar of *Hemerocallis*.

1. 'VER00323' exhibits flowers that are salmon orange in color with yellow-green throats.

2. 'VER00323' exhibits an everblooming habit; blooming from June to October in The Netherlands.
3. 'VER00323' exhibits a dormant plant habit.
4. 'VER00323' commences bloom early in the season.

The new cultivar can be most closely compared to the *Hemerocallis* cultivars 'VER00213' (U.S. Plant Pat. No. 26,605) and *Hemerocallis* 'VER00204' (U.S. Plant Pat. No. 26,606). 'VER00213' is similar to 'VER00323' in having a two-toned flower color, in having a light colored midrib on the petals, in having a dormant plant habit and an extended flowering period. 'VER00213' differs from 'VER00323' in having a shorter plant habit and in having a trumpet shaped flower that opens less with tepals that are not curved backwards. 'VER00204' is similar to 'VER00323' in having a two-toned flower color, in having a light colored midrib on the petals, in having a dormant plant habit and an extended flowering period. 'VER00204' differs from 'VER00323' in commencing bloom earlier in the season, in having larger flowers that are larger and more orange in color.

BRIEF DESCRIPTION OF THE DRAWINGS

The accompanying colored photographs illustrate the overall appearance and distinct characteristics of the new *Hemerocallis*. The photographs were taken of a 5 month-old plant of the new cultivar as field grown in Noordwijk, The Netherlands and place in a container for the photographs.

The photograph in FIG. 1 provides a side view of 'VER00323' in bloom.

Figure 1:
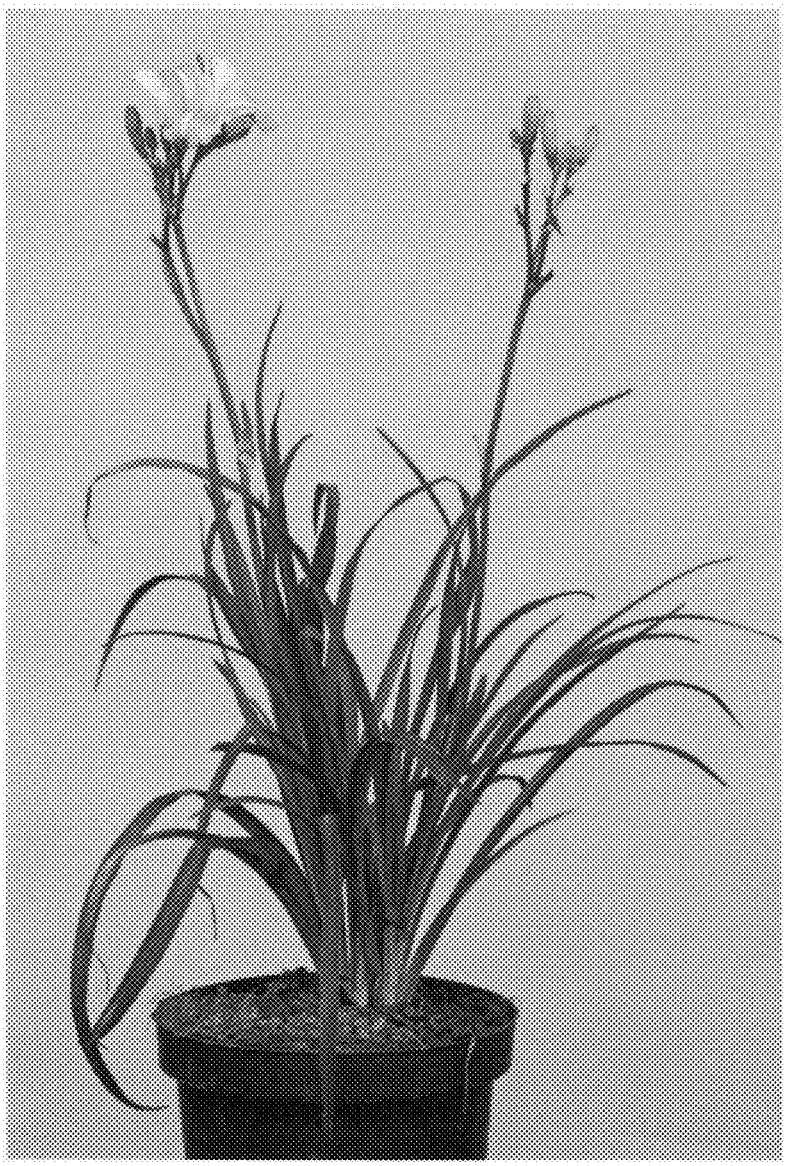
Figure 2:
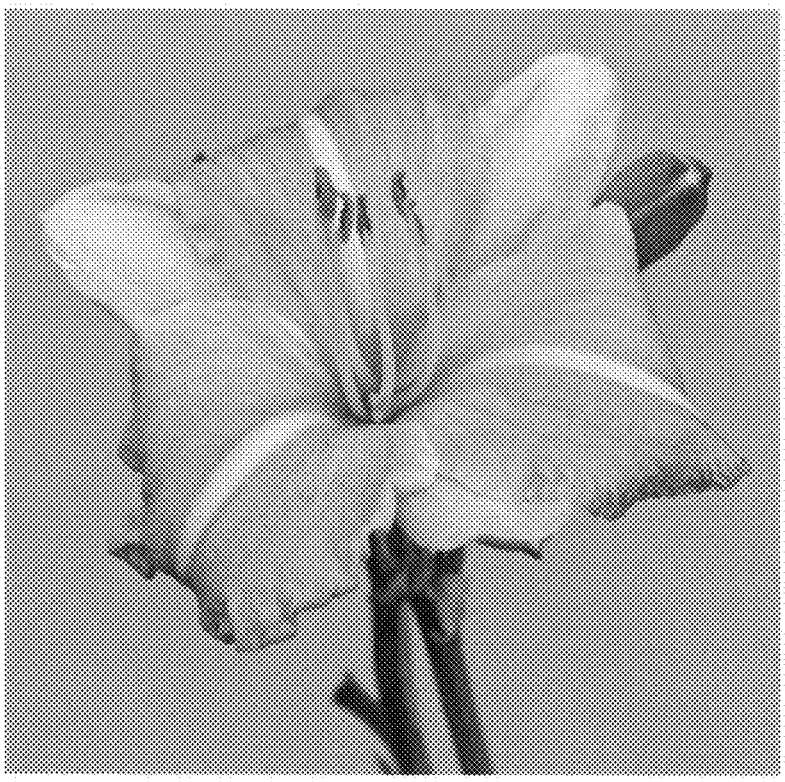

The photograph in FIG. 2 provides a close-up view of a flower of 'VER00323'.

Figure 3:
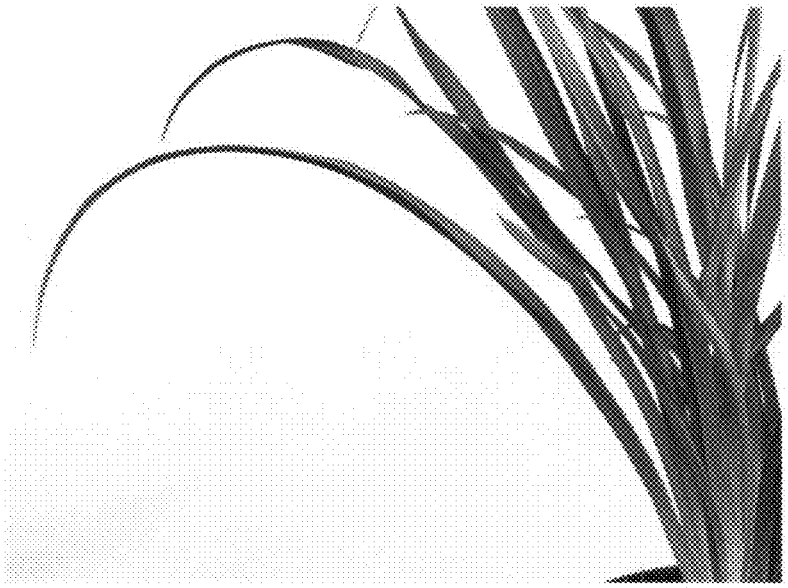

The photograph in FIG. 3 provides a close-up view of the foliage of 'VER00323'.

The colors in the photographs are as close as possible with the digital photography and printing techniques utilized and the color codes in the detailed botanical description accurately describe the new *Hemerocallis*.

DETAILED BOTANICAL DESCRIPTION OF THE PLANT

The following is a detailed description of 5 month-old plants of the new cultivar as field grown in Noordwijkerhout, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period*.—June to October in The Netherlands.

*Plant type*.—Herbaceous perennial.

*Plant habit*.—Upright with flowers held above the foliage, dormant type.

*Height and spread*.—Reaches about 40 cm in height and 50 cm in spread (2 year-old plant in the landscape).

*Hardiness*.—At least in U.S.D.A. Zone 5.

*Diseases*.—No particular susceptibility or resistance has been observed.

*Root description*.—Fleshy with fibrous secondary roots.

*Propagation*.—Division and tissue culture.

*Growth rate*.—Moderate, 4 months to fully root a single fan division in a 18-cm container and 8 months to produce a No. 1 division in the field from a single fan.

Foliage description:

*Leaf shape*.—Linear, moderately carinate and curved.

*Leaf division*.—Simple.

*Leaf base*.—Decurrent.

*Leaf apex*.—Long acuminate with a short apiculate outer tip.

*Leaf venation*.—Parallel, color upper surface; 137B, color lower surface; 143A.

*Leaf margins*.—Entire, very slightly undulate.

*Leaf attachment*.—Decurrent, no petioles.

*Leaf arrangement*.—Basal rosette.

*Leaf orientation*.—Held upright to slightly pendulant.

*Leaf surface*.—Both surfaces glabrous, upper surface slightly glossy, lower surface matte.

*Leaf color*.—Young leaves upper surface; color between 143A, young leaves lower surface; 143A, mature leaves upper surface; 137B mature leaves lower surface; between 137B and 143A.

*Leaf size*.—Up to 42.6 cm in length, an average of 1.6 cm in width.

*Leaf quantity*.—Average of 11 per rosette.

Flower description:

*Inflorescence type*.—Scape bearing a panicle of single flowers.

*Inflorescence size*.—Varies with opening of flowers, an average of 11.3 cm in width and 12.3 cm in height.

*Lastingness of flowers*.—About 24 hours, self cleaning.

*Flower size*.—An average of 9 cm in depth and 10.2 cm in diameter.

*Flower fragrance*.—None.

*Flower shape*.—Campanulate.

*Flower number*.—Average of 21.

*Flower aspect*.—Upright to outward.

*Flower bud*.—Oblanceolate in shape, average of 4.6 cm in length and 1 cm in diameter, color N144A and 151A with apex 144A to 144B.

*Rate of flower opening*.—Approximately 10% of flowers open at a time, average of 4 weeks for all flowers to open per scape.

*Flower attachment*.—Petiolate.

*Petals*.—3, obovate in shape, average of 9.2 cm in length and 4.6 cm in width, both surfaces are glabrous and moderately velvety, margins entire and slightly crinkled, apex retuse, base fused (lower 24%), color of upper surface when opening and fully open; 31C, base 1A and 2B, petal has a narrow axial stripe 11C, tube N144D, color of lower surface when opening and fully open; 14D, fading to 37C towards the margin, base 2A, tube N144C.

*Sepals*.—3, rotate in arrangement, average of 6.1 cm in length, 2.2 cm in width, oblanceolate in shape, entire margins, base is cuneate and fused 25%, acute apex, color upper surface young and mature; 16C, fading towards margins 22C and 24C, tube N144D, color lower surface young; 13A to 13B, base N144B, tube N144C, color lower surface mature; 13A to 13B and tinged with N144B, base N144B, tube N144C.

*Calyx*.—Rotate in shape, average of 6.2 cm in length and 9.6 cm in diameter.

*Peduncles*.—Slightly angled in shape, glabrous surface, average of 56.7 in length and 5 mm in diameter, average of 75° to soil level (=0°), strong, color 138A to 138B.

*Pedicels*.—Average of 3 mm in length and diameter, glabrous surface, round in shape, strong, held at an average angle of 35° to the peduncle (=0°), color is 143C.

Reproductive organs:

*Gynoecium*.—Pistil; 1, average of 8.4 cm in length, style; 8.35 cm in length, 25D, 150D at the base in color, stigma; crested, 11D in color, ovary; oblong in shape, 143C in color.

*Androecium*.—Stamens; 6, anthers; dorsifixed and narrow oblong in shape, 6 mm in length and 200A to 203A in color; filament; 4.9 cm in length, 14C in color, pollen; abundant in quantity and 17A in color.

*Fruit/seeds*.—None observed.

It is claimed:

1. A new and distinct cultivar of *Hemerocallis* plant named 'VER00323' as herein illustrated and described.

* * * * *